United States Patent
Bacque et al.

(10) Patent No.: US 6,762,196 B2
(45) Date of Patent: Jul. 13, 2004

(54) USE OF 2-AMINO-4-PYRIDYLMETHYL-THIAZOLINE DERIVATIVES AS INHIBITORS OF INDUCIBLE NO-SYNTHASE

(75) Inventors: Eric Bacque, Gif sur Yvette (FR); Antony Bigot, Massy (FR); Jean-Christophe Carry, Saint Maur des Fosses (FR); Serge Mignani, Chatenay-Malabry (FR); Baptiste Ronan, Clamart (FR); Michel Tabart, La Norville (FR)

(73) Assignee: Aventis Pharma S. A., Antony Cedex (FR)

( * ) Notice: Subject to any disclaimer, the term of this patent is extended or adjusted under 35 U.S.C. 154(b) by 0 days.

(21) Appl. No.: 10/290,624

(22) Filed: Nov. 8, 2002

(65) Prior Publication Data

US 2003/0153605 A1 Aug. 14, 2003

Related U.S. Application Data

(60) Provisional application No. 60/352,978, filed on Jan. 30, 2002.

(30) Foreign Application Priority Data

Nov. 9, 2001 (FR) ............................................ 01 14508

(51) Int. Cl.$^7$ .................. A61K 31/4436; C07D 409/06
(52) U.S. Cl. .................................... 514/342; 546/270.7
(58) Field of Search ........................ 546/270.7; 514/342

(56) References Cited

FOREIGN PATENT DOCUMENTS

| WO | WO 94/12165 | 6/1994 |
| WO | WO 95/11231 | 4/1995 |
| WO | WO 96/14842 | 5/1996 |

OTHER PUBLICATIONS

Luz Cardona et al., Synthesis of Natural Polyhydroxstibenes, Tetrahedron (1986, pp. 2725–2730, vol. 42, No. 10).

Singer M, et al, Synthesis of (R)–and (S)–4'–Acetoxyolivetol [(R)–and (S)–5–(4'Acetoxypentyl)–1,3–benzenediol]: Key Intermediated in the Synthesis of Tetrahydrocannabinol Derivatives, Synthesis, 1994, pp. 486–488.

Paul I. Creeke et al., Synthesis and Elaboration of Helerocycles Via Iodocyclisation of Unsaturated Thioureas, Tetrahedron (1989, pp. 4435–4438, vol. 30, No. 33).

Roger L. N Harris et al., Potential Wool Growth Inhibitors. 2(1H)–Pyridone Analogues of Mimosine, Aust. J. Chem. (1977, pp. 649–655, vol. 30).

Salvador Moncada et al., Biosynthesis of Nitric Oxide From L–Arginine A Pathway for the Regulation of Cell Function and Communication, Biochemical Pharmacology, vol. 38, No. 11, 1989, pp. 1709–1715.

Hudlicky Milos, Oxidations In Organic Chemistry, (1990, pp. 250–264, vol. 186).

*Primary Examiner*—Patricia L. Morris
(74) *Attorney, Agent, or Firm*—James W. Bolcsak

(57) ABSTRACT

The present invention relates to the use of 2-amino-4-pyridylmethyl thiazoline derivatives of formula (I)

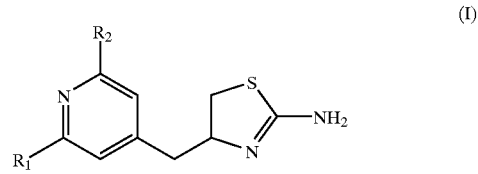

(I)

wherein either $R_1=R_2=Cl$ or $(C_1-C_4)$alkyl, or hydroxy; or $(C_1-C_4)$alkoxy or at least one of $R_1$ or $R_2$ is a hydrogen and the other is a $(C_1-C_4)$alkyl, hydroxy, $(C_1-C_4)$alkoxy or chlorine or pharmaceutically acceptable salts thereof as inhibitors of inducible NO-synthase.

10 Claims, No Drawings

USE OF 2-AMINO-4-PYRIDYLMETHYL-THIAZOLINE DERIVATIVES AS INHIBITORS OF INDUCIBLE NO-SYNTHASE

This application claims the benefit of U.S. Provisional Application No. 60/352,978, filed Jan. 30, 2002, which claims the benefit of priority of French Patent Application No. 01/14,508, filed Nov. 09, 2001.

The present invention relates to the use of 2-amino-4-pyridylmethyl thiazoline derivatives of formula (I):

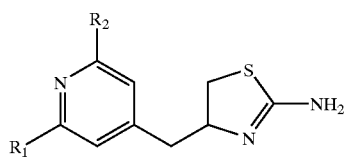

or pharmaceutically acceptable salts thereof as inhibitors of inducible NO-synthase.

The subject of the invention is the use of 2-amino-4-pyridylmethyl thiazoline derivatives of formula (I) and pharmaceutically acceptable salts thereof for the preparation of pharmaceutical compositions intended for preventing and treating diseases in which an abnormal production of nitric oxide (NO) by induction of inducible NO-synthase (NOS-2 or iNOS) is involved, the pharmaceutical compositions containing the novel 2-amino-4-pyridylmethyl-thiazoline derivatives and the pharmaceutically acceptable salts thereof and the novel 2-amino-4-pyridylmethyl-thiazoline derivatives and pharmaceutically acceptable salts thereof.

Nitric oxide (NO) is a diffusable radical involved in many physiological and pathological processes. It is synthesized by oxidation of L-Arginine, a reaction catalyzed by a family of enzymes known as nitric oxide synthases or NO-Synthases (NOSs), referenced in the international enzyme nomenclature under the number E.C. 1.14.13.39.

Three NOS isoforms, two of which are constitutive and one inducible, are known:
- a neuronal NOS (NOS-1 or nNOS) was originally isolated and cloned from nerve tissue in which it is a constitutive enzyme. The NOS-1 produces NO in response to various physiological stimuli such as the activation of membrane receptors according to a mechanism dependent on calcium and on calmodulin.
- an inducible NOS (NOS-2 or iNOS) can be induced in response to immunological stimuli such as, for example, cytokines or bacterial antigens in various cells such as, for example, macrophages, endothelial cells, hepatocytes, glial cells, as well as many other types of cells. This isoform activity is not regulated by calcium. Consequently, once induced, it produces a large amount of NO over prolonged periods.
- an endothelial NOS (NOS-3 or eNOS) is constitutive and calcium/calmodulin dependent. It was originally identified in vascular endothelium cells, in which it generates NO in response to physiological stimuli such as the activation of membrane receptors.

The NO produced by the neuronal endothelial constitutive isoforms (NOS-1 and NOS-3) is generally involved in intercellular signalling functions. For example, the endothelial cells which line the inner wall of blood vessels induce the relaxation of the underlying smooth muscle cells via the production of NO. It thus contributes towards regulating the arterial pressure.

The NO produced in large amount by the inducible isoform NOS-2 is, inter alia, involved in the pathological phenomena associated with acute and chronic inflammatory processes in a large variety of tissues and organs.

An excessive production of NO by induction of NOS-2 thus plays a part in degenerative pathologies of the nervous system such as, for example, multiple sclerosis, focal or global cerebral ischemia, cerebral or spinal trauma, Parkinson's disease, Huntington's disease, Alzheimer's disease, amyotrophic lateral sclerosis, migraine, depression, schizophrenia, anxiety, epilepsy. Similarly, aside the central nervous system, the induction of NOS-2 is involved in many pathologies with inflammatory components such as, for example, diabetes, atherosclerosis, myocarditis, arthritis, arthrosis, asthma, inflammatory bowel diseaese, Crohn's disease, peritonitis, gastroesophageal reflux, uveitis, Guillain-Barré syndrome, glomerulo-nephritis, lupus erythematosus and psoriasis. The NOS-2 was also involved in the growth of certain forms of tumors such as, for example, epitheliomas, adenocarcinomas or sarcomas, and in infections with Gram-positive or Gram-negative intracellular or extracellular bacteria.

In all the situations in which an overproduction of NO is deleterious, it thus appears to be desirable to reduce the production of NO by administering substances capable of inhibiting the NOS-2. However, given the important physiological roles played by the constitutive isoform NOS-3, in particular, in regulating the arterial pressure, it is essential that the inhibition of the isoform NOS-2 has the least possible effect on the isoform NOS-3. Actually, it is known that the administration of unselective inhibitors of NOS isoforms leads to vasoconstriction and an increase in arterial pressure (Moncada, S., Palmer, R. M. J. and Higgs, E. A., Biosynthesis of nitric oxide from L-arginine: a pathway for the regulation of cell function and communication, *Biochem. Pharmacol.*, 1989, 38: 1709–1715). These effects on the cardiovascular system are deleterious since they reduce the supply of nutrients to the tissues. Consequently, the present invention relates to compounds whose inhibitory activity with respect to NOS-2 is significantly higher than their inhibitory activity with respect to NOS-3.

Thiazoline-based NOS inhibitors are described in particular in patent applications WO94/12165, WO95/11231 and WO96/14842.

Thus in accordance with the present invention there is provided a series of 2-amino-4-pyridylmethyl-thiazoline derivatives of formula (I):

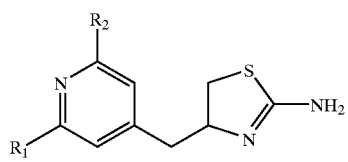

wherein either $R_1$, $R_2$ are identical and represent an hydroxy radical, $(C_1-C_4)$alkyl, chlorine or $(C_1-C_4)$ alkoxy; or at least one of $R_1$ or $R_2$ is hydrogen and the other is a $(C_1-C_4)$ alkyl radical, $(C_1-C_4)$ alkoxy, hydroxy or chlorine. The present invention also provides the preparation of useful medicinal products comprising a compound of formula (I) for preventing or treating the diseases in which an abnormal production of nitric oxide (NO) by induction of inducible NO-synthase (NOS-2 or iNOS) is involved.

In the above definitions and in those which follow, the $(C_1-C_4)$alkyl radical and $(C_1-C_4)$alkoxy contain 1 to 4 carbon atoms in straight or branched chain.

The compounds of formula (I) contain one or more asymmetric carbons and can thus be in racemic form or in the form of enantiomers and diastereoisomers; these also form a part of the invention as well as the mixtures thereof.

Moreover, the compounds of formula (I) can be in the tautomeric form (Ia):

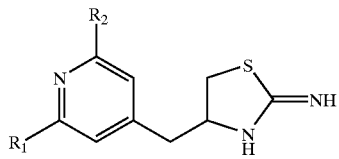

(Ia)

These tautomers also form a part of the invention.

Among the compounds of formula (I) useful according to the invention, mention may be made of the following compounds:

4-(2-hydroxy-pyridin-4-ylmethyl)-4,5-dihydro-1,3-thiazol-2-ylamine, 4-(2-chloro-pyridin-4-ylmethyl)-4,5-dihydro-1,3-thiazol-2-ylamine, and 4-(2,6-dichloro-pyridin-4-ylmethyl)-4,5-dihydro-1,3-thiazol-2-ylamine.

Also included as part of this invention are the racemates, enantiomers, diastereoisomers thereof and the tautomers thereof, as well as pharmaceutically acceptable salts thereof, and more particularly the following compounds:

(+)-4-(2-hydroxy-pyridin-4-ylmethyl)-4,5-dihydro-1,3-thiazol-2-ylamine, 4-(2-chloro-pyridin-4-ylmethyl)-4,5-dihydro-1,3-thiazol-2-ylamine, 4-(2,6-dichloro-pyridin-4-ylmethyl)-4,5-dihydro-1,3-thiazol-2-ylamine, and the tautomers thereof, as well as the pharmaceutically acceptable salts thereof.

Among the compounds of formula (I) useful according to the invention and particularly preferred, mention may be made of the following compound:

4-(2-hydroxy-pyridin-4-ylmethyl)-4,5-dihydro-1,3-thiazol-2-ylamine, and the racemates, enantiomers thereof and tautomers thereof, as well as the pharmaceutically acceptable salts thereof, and most particularly the following compound:

(+)-4-(2-hydroxy-pyridin-4-ylmethyl)-4,5-dihydro-1,3-thiazol-2-ylamine, and the tautomer thereof as well as the pharmaceutically acceptable salts thereof.

The invention also relates to the pharmaceutical compositions containing, as active principle, a derivative of formula (I) for which either $R_1$, $R_2$ are identical and represent an hydroxy radical, a ($C_1$–$C_4$) alkyl, a chlorine, or a ($C_1$–$C_4$) alkoxy; or at least one of $R_1$ or $R_2$ is an hydrogen and the other is a ($C_1$–$C_4$) alkyl radical, ($C_1$–$C_4$) alkoxy, hydroxy or chlorine as well as the racemates, enantiomers, diastereoisomers thereof and mixtures thereof, tautomers thereof and pharmaceutically acceptable salts thereof.

The compounds of formula (I) can be prepared by cyclization of a derivative of formula:

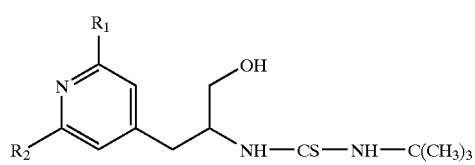

(II)

in which $R_1$ and $R_2$ have the same meanings as in formula (I) as defined above.

This cyclization is generally carried out using an acid such as hydrochloric acid, in an aqueous medium, at a temperature of about 100° C. 6N hydrochloric acid is preferably used.

The derivative of formula (II) can be obtained according to the following reaction schemes:

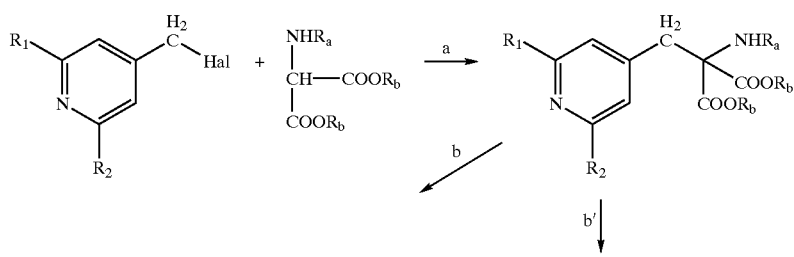

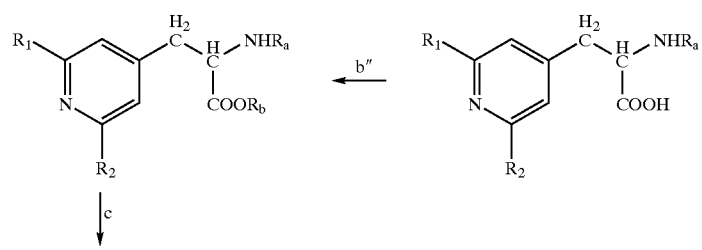

-continued

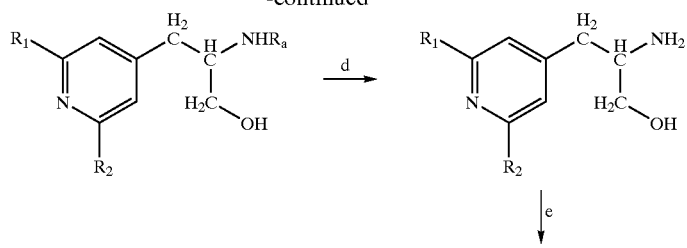

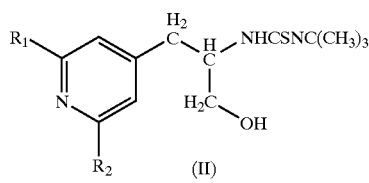

In these formulae $R_a$ is a protecting group of the amine function such as those described by T. W. GREENE, *Protective groups in Organic Synthesis, J. Wiley-Interscience Publication* (1991), preferably an acetyl or tert-butoxycarbonyl radical, $R_b$ is a ($C_1$–$C_4$) alkyl or alkoxycarbonyl radical, preferably, methyl, ethyl or isobutyloxycarbonyl and Hal is an halogen atom, preferably, chlorine, bromine or iodine.

The reaction a is generally carried out in the presence of a sodium ($C_1$–$C_4$) alkoxide (preferably sodium ethoxide), in the corresponding alcohol, at a temperature of between 10° C. and the the boiling point of the reaction medium.

The reaction b is generally carried out in an inert solvent such as dimethylformamide in the presence of lithium iodide, at a temperature of between 100° C. and the boiling point of the reaction medium or in a ($C_1$–$C_4$) aliphatic alcohol in the presence of sodium hydroxide at a temperature of between 10° C. and 30° C., followed by neutralizing with aqueous HCl (preferably 6N to 12N) then heating in a solvent such as dioxane or ($C_1$–$C_4$) aliphatic alcohol at a temperature of the boiling point of the reaction medium.

The reaction b' is preferably carried out using 12 N hydrochloric acid at a temperature of about 100° C.

The reaction b" for the derivatives for which Rb is an alkyl radical is generally carried out by the action of a ($C_1$–$C_4$) aliphatic alcohol (preferably methanol or ethanol), in the presence of an inorganic acid such as sulfuric acid at a temperature of between 50° C. and the the boiling point of the reaction medium. For the derivatives for which $R_b$ is an isobutyloxycarbonyl radical, this reaction is generally carried out by the action of isobutyl chloroformate in the presence of a base such as triethylamine, in an inert solvent such as tetrahydrofuran at a temperature of between –20° C. and 0° C.

The reduction reaction c is preferably carried out using an hydride such as sodium borohydride or lithium aluminum hydride in a ($C_1$–$C_4$) aliphatic alcohol or tetrahydrofuran, at a temperature of between 10° C. and 30° C.

The deprotection reaction d for the compounds for which $R_a$ is a protecting group of the amine function is carried out by any method of deprotection known by those skilled in the art and particularly those described by T. W. GREENE, *Protective groups in Organic Synthesis, J. Wiley-Interscience Publication* (1991). Preferably, when the protecting group is an acetyl radical, this reaction is carried out using aqueous hydrochloric acid at a temperature of about 100° C. When the the protecting group is a tert-butoxycarbonyl radical, this reaction is carried out using hydrochloric acid in dioxane, at a temperature of about 20° C.

The reaction e is carried out by the action of tert-butyl isothiocyanate, in an inert solvent such as ($C_1$–$C_4$) aliphatic alcohol (preferably methanol or ethanol), optionally in the presence of a tertiary amine such as triethylamine, at a temperature of between 20° C. and the boiling point of the reaction medium.

The compound of formula (II) for which $R_1$ and $R_2$ are OH can be prepared by the same action from the compounds of formula (III) for which Z is a silyl radical, preferably tert-butyldimethylsilyl, the preparation is described in *Synthesis* 1994, 486 and *Tetrahedron* 1986, 42, 2725.

The compoud of formula (I) for which $R_1$ is OH and $R_2$ is hydrogen may be prepared according to the following reaction scheme:

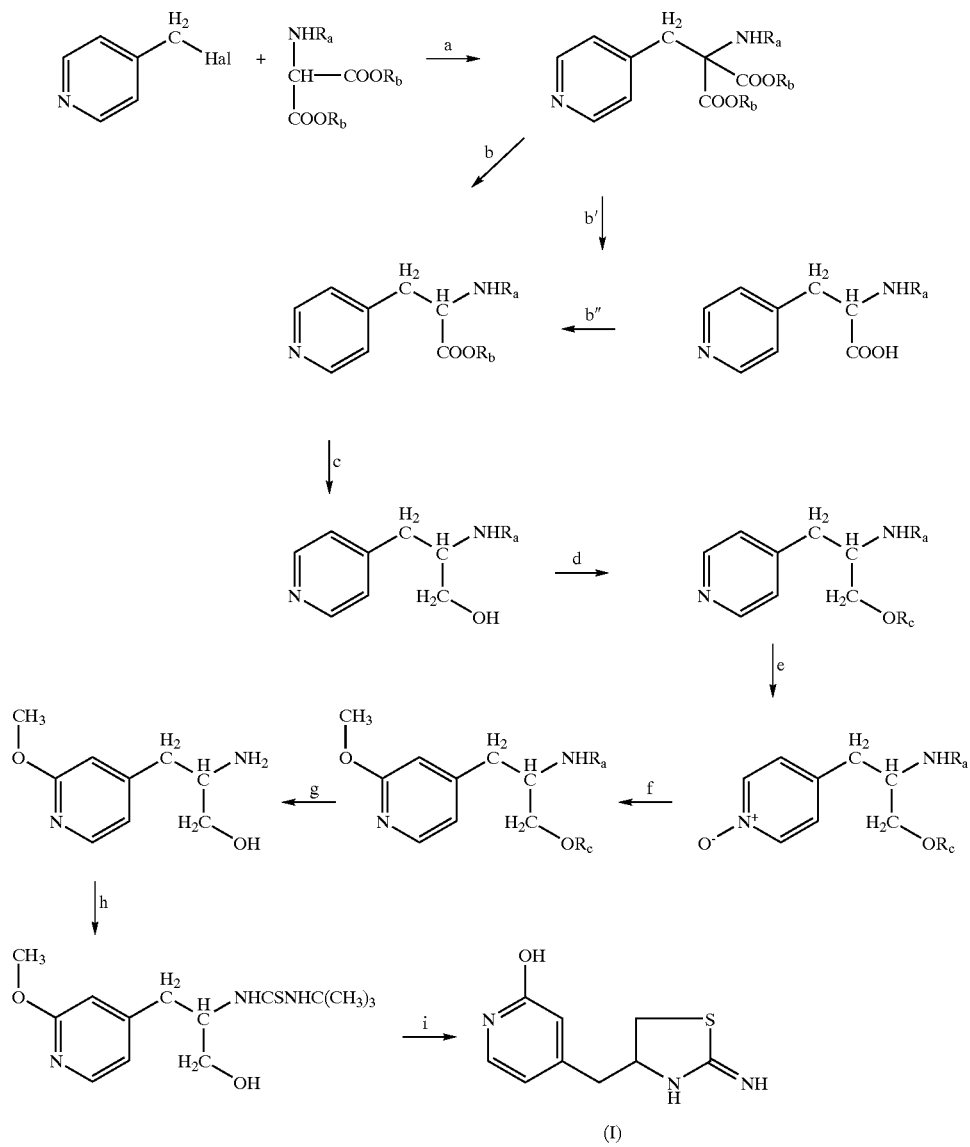

(I)

In these formulae $R_a$ is a protecting group of the amine function such as those described by T. W. GREENE, *Protective groups in Organic Synthesis, J. Wiley-Interscience Publication* (1991), preferably an acetyl or tert-butoxycarbonyl radical and $R_b$ is a $(C_1-C_4)$ alkyl or alkoxycarbonyl radical, preferably, methyl, ethyl or isobutyloxycarbonyl. $R_c$ is a protecting group of the alcohol function such as those described by T. W. GREENE, *Protective groups in Organic Synthesis, J. Wiley-Interscience Publication* (1991), preferably a silyl and most particularly tert-butyldimethylsilyl radical.

The reaction a is generally carried out in the presence of a sodium $(C_1-C_4)$ alkoxide (preferably sodium ethoxide), in the corresponding alcohol at a temperature of between 10° C. and the boiling point of the reaction medium.

The reaction b is generally carried out in an inert solvent such as the dimethylformamide in the presence of lithium iodide, at a temperature of between 100° C. and the boiling point of the reaction medium or in $(C_1-C_4)$ aliphatic alcohol, in the presence of sodium hydroxide, at a temperature of between 10 and 30° C. followed by neutralizing with an aqueous 6N HCl then heating in an inert solvent such as dioxane or alcohol such as ethanol at the boiling point temperature of the reaction medium.

The reaction b' is preferably carried out using 12 N hydrochloric acid, at a temperature of about 100° C.

The reaction b" for the derivatives for which $R_b$ is an alkyl radical is generally carried out by the action of a $(C_1-C_4)$ aliphatic alcohol (preferably methanol, ethanol), in the presence of an inorganic acid such as sulfuric acid at a temperature of between 50° C. and the the boiling point of the reaction medium. For the derivatives for which $R_b$ is an isobutyloxycarbonyl radical, this reaction is generally carried out by the action of isobutyl chloroformate in the presence of a base such as triethylamine, in an inert solvent such as tetrahydrofuran at a temperature of between −20° C. and 0° C.

The reduction reaction c is preferably carried out using a hydride such as sodium borohydride or lithium borohydride in a $(C_1-C_4)$ aliphatic alcohol and/or tetrahydrofuran, at a temperature range of from about 10° C. to about 30° C.

The protection reaction d is carried out by any of the hitherto known method of protection of the alcohol function such as those described by T. W. GREENE, *Protective groups in Organic Synthesis*, J. Wiley-Interscience Publication (1991), preferably using tert-butyldimethylsilyl chloride in the presence of a base such as tertiary amine (preferably diisopropylethylamine), in a solvent such as dichloromethane, at a temperature range of from about 0° C. to about 30° C.

The reaction e is carried out in the presence of 3-chloroperoxybenzoïc acid, in a solvent such as dichloromethane at a temperature of between 0° C. and the boiling point of the reaction medium.

The reaction f is carried out in the presence of paratoluenesulfonyl chloride in the presence of a base such as tertiary amine (preferably triethylamine), in a solvent such as alcohol (preferably methanol) at a temperature of between 10° C. and the boiling point of the reaction medium.

The deprotection reaction g for the compounds for which $R_a$ is a protecting group of the amine function and $R_c$ is a protecting group of the alcohol function is carried out by any method of deprotection known by those skilled in the art and particularly those described by T. W. GREENE, *Protective groups in Organic Synthesis*, J. Wiley-Interscience Publication (1991). Preferably, when the protecting group $R_a$ is an acetyl radical and when the the protecting group $R_c$ is silyl and most particularly tert-butyldimethylsilyl radical, this is carried out using aqueous hydrochloric acid (preferably HCl 6N) at the boiling point temperature of the reaction medium.

The reaction h is carried out by the action of tert-butyl isothiocyanate, in an inert solvent such as $(C_1-C_4)$ aliphatic alcohol (preferably methanol, ethanol), optionally in the presence of a tertiary amine such as triethylamine, at a temperature of between 20° C. and the boiling point of the reaction medium.

The reaction i is generally carried out using an acid such as hydrochloric acid, in aqueous medium, at the boiling point temperature of the reaction medium. 6N hydrochloric acid is preferably used.

The compounds of formula (I) for which either $R_1$ is OAlk and $R_2$ is hydrogen, or $R_1$ and $R_2$ are OAlk can be respectively prepared from compounds of formula (I) for which either $R_1$ is OH and $R_2$ is hydrogen, or $R_1$ and $R_2$ are OH, by alkylation with a compound of structure Hal—Alk. Hal represents an halogen atom (preferably chlorine, bromine or iodine) and Alk has the same meaning as in formula (I). This reaction is generally carried out in an inert solvent such as dimethylformamide, dimethylsulfoxide, dioxane, tetrahydrofuran in the presence of an acid acceptor such as trialkylamine (triethylamine for example), alkali metal hydroxide (sodium hydroxide, potassium hydroxide for example) or an alkali metal hydride (sodium hydride for example), at a temperature of between 20° C. and the boiling point of the reaction medium.

The compounds of formula (I) are isolated and can be purified by the commonly known methods, for example by crystallization, chromatography or extraction.

The enantiomers of the compounds of formula (I) can be obtained by resolving the racemic mixtures, for example by chromatography on a chiral column according to PIRCKLE W. H. et al., *Asymmetric Synthesis, vol. 1, Academic Press* (1983) or by formation of salts or by synthesis from chiral precursors. The diastereoisomers can be prepared according to the known conventional methods (crystallization, chromatography or from chiral precursors).

The compounds of formula (I) may optionally be converted into addition salts with an inorganic or organic acid by the action of such an acid in an organic solvent such as an alcohol, a ketone, an ether or a chlorinated solvent. These salts also form a part of the invention.

Examples of pharmaceutically acceptable salts which may be mentioned are the following salts: benzenesulfonate, hydrobromide, hydrochloride, citrate, ethanesulfonate, fumarate, gluconate, iodate, isethionate, maleate, methanesulfonate, methylenebis-β-oxynaphtoate, nitrate, oxalate, pamoate, phosphate, salicylate, succinate, sulfate, tartrate, theophyllinacetate and p-toluenesulfonate.

The compounds of formula (I) are inhibitors of NO-synthase inducible or NO-synthase of type 2 (NOS-2) and are thus useful for preventing and treating disorders associated with an excessive NO production such as mutiple sclerosis, focal or global cerebral ischemia, cerebral or spinal trauma, Parkinson's disease, Huntington's disease, Alzheimer's disease, amiotrophic lateral scherosis, migraine, depression, schizophrenia, anxiety, epilepsy, diabetes, atherosclerosis, myocarditis, arthritis, arthrosis, asthma, inflammatory bowel disease, Crohn's disease, peritonitis, gastro-esophageal reflux, uveitis, Guillain-Barré syndrome, glomerulo-nephritis, lupus erythematosus and psoriasis, the growth of certain forms of tumors such as for example epitheliomas, adenocarcinomas or sarcomas, and infections with Gram-positive or Gram-negative intracellular or extracellular bacteria.

Their activities as inhibitors of NOS-2 and NOS-3 were determined by measuring the conversion of $[^3H]$-L-arginine into $[^3H]$-L-citrulline with, respectively, a NOS-2 enzymatic fraction extracted from the lungs of rats or mice pretreated with lipopolysaccharides (10 mg/kg i.p. 6 hours before collecting the tissue) and with a commercial preparation of recombinant bovine NOS-3. The compounds were incubated for 20 to 30 minutes at 370° C. in the presence of 5 $\mu$M (for NOS-2 activity) or 10 $\mu$M (for NOS-3 activity) of $[^3H]$-L-arginine, 1 mM of NADPH, 15 $\mu$M of tetrabiopterine, 1 $\mu$M of FAD, 0.1 mM of DTT in a HEPES buffer (50 mM, pH 6.7) containing 10 $\mu$g/ml of calmoduline and 1.25 mM of $CaCl_2$ when the NOS-3 activity was measured. The incubation was stopped by adding cold HEPES buffer (100 mM, pH 5.5) containing 10 mM EGTA and 500 mg of cationic ion-exchange resin (AG50W-X8, counter-ion: $Na^+$) to separate the $[^3H]$-L-arginine from the $[^3H]$-L-citrulline. After separation of the phases by settling for 5 min, the radioactivity remaining in the liquid phase was measured in a scintillation counter in the presence of a suitable scintillating liquid. The yield for the recovery of the formed L-$[^3H]$citrulline was able to be estimated using L-[ureido-$^{14}C$]-citrulline as external standard.

The activity NOS-2 or NOS-3 was expressed in picomole (s) of $[^3H]$-L-citrulline formed per minute and per milligram of protein contained in the reaction medium.

In this test on the enzyme NOS-2, the $IC_{50}$ value for the compounds of formula (I) is less than or equal to 10 $\mu$M.

The selectivity is measured by the $IC_{50}$ NOS-3/$IC_{50}$ NOS-2 ratio. This selectivity is greater than 45.

The compounds of formula (I) are of low toxicity. Their $LD_{50}$ is greater than 40 mg/kg via cutaneous route in mice.

The following example illustrates the invention in a non exhaustive manner.

EXAMPLE 1

(+)-4-(2-Hydroxy-pyridin-4-ylmethyl)-4,5-dihydro-thiazol-2-ylamine

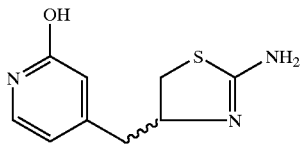

A suspension of 0.4 g of N-(tert-butyl)-N'-[2-hydroxy-1-(3-methoxy-pyridin-4-yl-methyl)ethyl]-thiourea in 4 mL of aqueous solution of 6N hydrochloric acid is heated at a temperature of about 100° C. for 18 hours. The reaction medium is then concentrated under reduced pressure (2 kPa) at a temperature of about 40° C. The residue obtained is taken up by 25 mL of distilled water and the mixture is washed with 2 times 20 mL of dichloromethane. The aqueous phase is evaporated under reduced pressure (2 kPa) at a temperature of about 40° C. The residue is taken up with 2 times 15 mL of ethanol and concentrated according to the conditions described above, then dried in an oven under reduced pressure (10 kPa) at a temperature of about 40° C. for 4 hours. About 0.31 g of racemic 4-(2-amino-4,5-dihydro-thiazol-4-ylmethyl)-1H-pyridin-2-one hydrochloride, are obtained in the form of a pale yellow solid melting at 124° C. This product is purified by chromatography on a column of CHIRALCEL OD 20μ in an heptane-ethanol-triethylamine mixture (80/20/0.1 by volume). The fractions containing the expected product are collected and concentrated under reduced pressure (1 kPa) at a temperature of about 40° C. and then the residue is dried in an oven under reduced pressure (10 kPa) at a temperature of about 40° C. About 0.0131 g of (+)-4-(2-Hydroxy-pyridin-4-ylmethyl)-4,5-dihydro-thiazol-2-ylamine, ($\alpha_D^{20°}$=+12.1+/−0.7 in the 0.5% DMSO) are obtained. [$^1$H NMR spectrum (300 MHz, (CD$_3$)$_2$SO d6, δ in ppm): 2.73 (dd, J=13.5 and 7 Hz, 1H); 2.80 (dd, J=13.5 and 7 Hz, 1H); 3.27 (dd, J=11.5 and 5.5 Hz, 1H); 3.62 (dd, J=11.5 and 7.5 Hz, 1H); 4.53 (mt, 1H); 6.13 (dd, J=6.5 and 1.5 Hz, 1H); 6.24 (s large, 1H); 7.34 (d, J=6.5Hz, 1H); from 8.90 to 9.40 (mf very broad, 2H); from 9.60 to 10.40 (mf very broad, 1H)].

N-(tert-Butyl)-N'-[2-hydroxy-1-(3-methoxy-pyridin-4-ylmethyl) ethyl]-thiourea

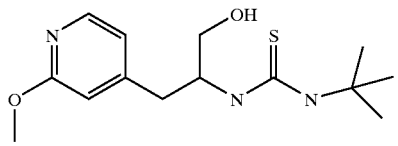

To a solution of 0.3 g of 2-amino-3-(3-methoxy-pyridin-4-yl)-1-propanol in 50 mL of absolute ethanol, about 0.337 mL of tert-butylisothiocyanate is added then the reaction medium is stirred under an inert atmosphere at a temperature of about 20° C. for 18 hours. About 0.337 mL of tert-butylisothiocyanate is added again and the reaction mixture is heated at a temperature of about 60° C. for 4 hours. After cooling, the reaction medium is concentred under reduced pressure (2 kPa) at a temperature of about de 40° C. The oil obtained is purified by chromatography under argon pressure (50 kPa), in a column of silica gel (particle size 40–63 μm; diameter 4 cm; height 22 cm), eluting with a 20% dichloromethane/methanol/aqueous ammonia mixture (90/10/0.5 by volume) and obtaining fractions of 10 mL. The fractions containing the expected product are collected and concentred under reduced pressure (2 kPa) at a temperature of about 40° C. About 0.4 g of N-(tert-butyl)-N'-[2-hydroxy-1-(3-methoxy-pyridin-4-yl-methyl)ethyl]-thiourea is obtained, under the form of an yellow oil. [Infrared spectrum CH$_2$Cl$_2$: 3620; 3411; 2972; 1614; 1561; 1532; 1400; 1319; 1161; 1041 and 815 cm$^{-1}$].

2-Amino-3-(3-methoxy-pyridin-4-yl)-1-propanol

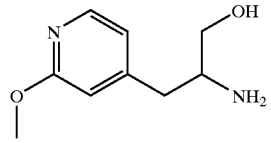

A mixture of 1.2 g of N-[1-(tert-butyl-dimethyl-silanyloxymethyl)-2-(3-methoxy-pyridin-4-yl)ethyl]-acetamide in 60 mL of aqueous solution of 6N hydrochloric acid is heated at a temperature of about 100° C. for 30 minutes. After cooling at a temperature of about 20° C., an adequate volume of an aqueous 30% sodium hydroxide solution is added dropwise to obtain a pH of about 10. The mixture is extracted with 3 times 100 mL of ethyl acetate and the organic extracts are combined, dried over magnesium sulfate then concentrated under reduced pressure (2 kPa) at a temperature of about 40° C. About 0.3 g of 2-amino-3-(3-methoxy-pyridin-4-yl)-1-propanol is obtained in the form of an yellow-colored oil. [Infrared spectrum CH$_2$Cl$_2$: 3628; 3335; 2948; 1614; 1561; 1400; 1319; 1162; 1044 et 815 cm$^{-1}$].

N-[1-(tert-Butyl-dimethyl-silanyloxymethyl)-2-(3-methoxy-pyridin-4-yl)ethyl]-acetamide

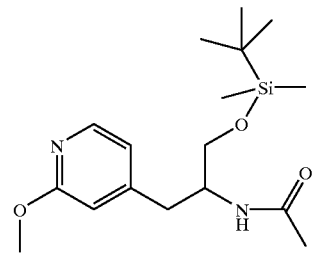

To a mixture of 5.12 g of N-[1-(tert-butyl-dimethyl-silanyloxymethyl)-2-(1-oxy-pyridin-4-yl)ethyl]-acetamide in 150 mL of anhydrous methanol, about 6 g of p-toluene sulfonylchloride then 8.9 mL of triethylamine are added. The reaction medium is heated at a temperature of about 60° C. for 96 hours then concentrated under reduced pressure (2 kPa) at a temperature of about 40° C. The residue is taken up by 200 mL of dichloromethane and washed with 3 times 150 mL of distilled water and 100 mL of an aqueous saturated solution of sodium hydroxide chloride. The organic phase is dried over magnesium sulfate, filtered then concentrated under reduced pressure (2 kPa) at a temperature of about 40° C. The residue is purified by chromatography under argon pressure (50 kPa), on column of silica gel (particle size 40–63 μm; diameter 7 cm; height 30 cm), eluting with a 20% dichloromethane/methanol/aqueous ammonia mixture (95/5/0,5 by volume) and obtaining fractions of 10 mL. The fractions containing the expected product are combined and concentrated under reduced pressure (2 kPa) at a temperature of about 40° C. About 1.24 g of N-[1-(tert-butyl-dimethyl-silanyloxymethyl)-2-(3-methoxy-pyridin-4-yl)-ethyl]-acetamide is obtained in the form of an yellow oil. [Infrared spectrum CCl₄: 3446; 2954; 2930; 2858; 1684; 1614; 1562; 1499; 1399; 1255; 1117; 1043 and 837 cm⁻¹].

N-[1-(tert-Butyl-dimethyl-silanyloxymethyl)-2-(1-oxy-pyridin-4-yl)-ethyl]-acetamide

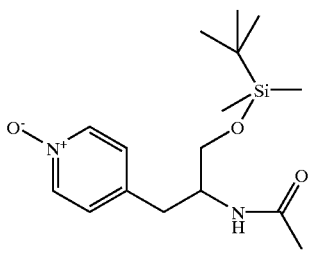

To a mixture of 21 g of N-[1-(tert-butyl-dimethyl-silanyloxymethyl)-2-(pyridin-4-yl)-ethyl]-acetamide in 250 mL of dichloromethane, while stirring under an inert atmosphere, about 9.4 g of 3-chloro-peroxy-benzoic acid is slowly added then heated at a temperature of about 40° C. for 30 minutes. Then the reaction medium is cooled and washed by 3 times 200 mL of a saturated sodium hydrogen carbonate solution then 150 mL of distilled water. The organic phase is dried over magnesium sulfate then concentrated under reduced pressure (2 kPa) at a temperature of about 40° C. The oil obtained is purified by chromatography under argon pressure (50 kPa), on a column of silica gel (particle size 40–63 µm; diameter 7 cm; height 37 cm), eluting with successive mixtures of 20% dichloromethane/methanol/aqueous ammonia (97/3/0.5, 95/5/0.5, 90/10/0.5 by volume) and obtaining fractions of 50 mL. The fractions containing the expected product are conbined and concentrated under reduced pressure (2 kPa) at a temperature of about 40° C. Thus 4.5 g of N-[1-(tert-butyl-dimethyl-silanyloxymethyl)-2-(1-oxy-pyridin-4-yl)-ethyl]-acetamide is obtained in the form of an yellow oil. [¹H NMR spectrum (300 MHz, (CD₃)₂SO d6, δ in ppm); 0.07 (s, 6H); 0.90 (s, 9H); 1.65 (s, 3H); 2.57 (dd, J=13.5 and 9.5 Hz, 1H); 2.85 (dd, J=13.5 and 4.5 Hz, 1H); from 3.40 to 3.60 (mt, 2H); 3.96 (mt, 1H); 7.22 (d, J=7 Hz, 2H); 7.73 (d, J=8 Hz, 1H); 8.12 (d, J=7 Hz, 2H).

N-[1-(tert-Butyl-dimethyl-silanyloxymethyl)-2-(pyridin-4-yl)-ethyl]-acetamide

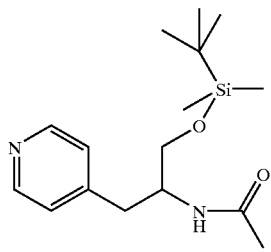

To a suspension of 25 g of N-(1-hydroxymethyl-2-(pyridin-4-yl)-ethyl)-acetamide in 700 mL of dichloromethane, with stirring, about 87 g of ter-butyldimethylsilyle is added and then 112 mL of diisopropylethylamine is added dropwise. The reaction medium is stirred for 24 hours at a temperature of about 20° C., then distilled water is added. After separation of the phases by settling, the organic phase is washed with 3 times 250 mL of distilled water and 200 mL of an aqueous saturated solution of sodium hydroxide. Then it is dried over over magnesium sulfate, filtered and concentrated under reduced pressure (2 kPa) at a temperature of about 40° C. The oil obtained is purified by chromatography under argon pressure (50 kPa) on a column of silica gel (particle size 40–63 µm; diameter 11 cm; height 40 cm), eluting with a 20% dichloromethane/methanol/aqueous ammonia mixture (95/15/0.5 by volume) and obtaining fractions of 100 mL. The fractions containing the expected product are combined and concentrated under reduced pressure (2 kPa) at a temperature of about 40° C. Thus 21 g of N-[1-(tert-butyl-dimethyl-silanyloxymethyl)-2-(pyridin-4-yl)-ethyl]-acetamide is obtained in the form of a white solid. [Mass spectrum DCI m/z=309 MH⁺]

N-(1-Hydroxymethyl-2-(pyridin-4-yl)-ethyl)-acetamide

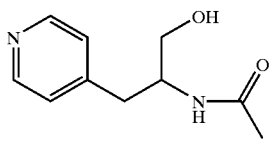

To a solution of 21.5 g of ethyl 2-(acetylamino)-3-(4-pyridinyl) propanoate in 800 mL of anhydrous methanol, with stirring under an inert atmosphere, about 8.7 g of sodium hydroxide borohydride is slowly added maintaining the temperature under 30° C. After the additon, the stiring of the reaction mediun is continued at a temperature of about 20° C. for about 24 hours, then is concentrated under reduced pressure (2 kPa) at a temperature of about 30° C. The residue is taken up by 450 mL of water and extracted with 4 times 150 mL of dichloromethane. The aqueous phase is concentrated under reduced pressure (2 kPa) at a temperature of about 50° C. The residue is purified by chromatography under argon pressure (50 kPa), on a column of silica gel (particle size 40–63 µm; diameter 7.5 cm; height 40 cm), eluting with a 20% dichloromethane/methanol/ammonia mixture (90/10/0.5 by volume) and obtaining fractions of 50 mL. The fractions containing the expected product are combined and concentrated under reduced pressure (2 kPa) at a temperature of about 40° C. Thus 2,6 g of N-(1-hydroxymethyl-2-(pyridin-4-yl)-ethyl)-acetamide is obtained in the form of a solidified oil. [IR spectrum (KBr): 3279; 3200; 2865; 1647; 1609; 1560; 1374; 1080; 1057; 1005; 907; 806; 566 and 517 cm⁻¹].

Ethyl 2-(acetylamino)-3-(4-pyridinyl)-propanoate

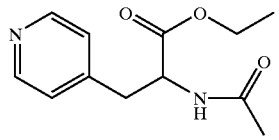

To a solution of 49.4 g of diethyl 2-(acetylamino)-2-(4-pyridinylmethyl)-malonate in 600 mL of absolute ethanol, about 51.2 mL of an aqueous 5N sodium hydroxide solution is added dropwise. The mixture is stirred for 1 hour at a temperature of about 20° C. then 21.3 mL of aqueous 12 N hydrochloric acid solution is added dropwise and the reaction medium is heated at a temperature of about 70° C. for 5 hours. After cooling at a temperature of about 20° C., the reaction mixture is concentrated under reduced pressure (2 kPa) at a temperature of about 50° C. The residue is taken up in 200 mL of cold ethanol and the precipitate formed therefrom is washed with 2 times 30 mL cold ethanol. The filtrate is evaporated following the conditions described above. This operation is repeated several times to remove sodium hydroxide from the reaction medium. Thus 43.1 g of 2-(acetylamino)-3-(4-pyridinyl)ethylpropanoate is obtained in the form of an yellow orange-colored oil. [Mass spectrum EI m/z=236 M$^+$; m/z=178 M—NHAc; m/z=121 $C_7H_9N_2^+$; m/z=93 $C_6H_7N^+$; peakof base m/z=43 $C_2H_3O^+$].

Diethyl 2-(acetylamino)-2-(4-pyridinylmethyl)-malonate

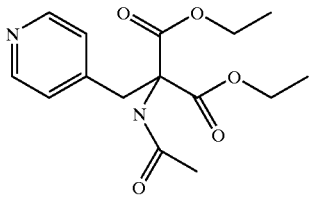

To 750 mL of ethanol, about 9 g of sodium hydroxide is added dropwise, while stirring under an inert atmosphere. After the addition of sodium hydroxide, the temperature of reaction mixture is maintained at about 20° C., and 42 g of diethyl acetamidomalonate is slowly added then the mixture is stirred at a temperature of about 20° C. for 1 hour and 30 minutes. A suspension of 61.5 g of 4-bromomethyl-pyridine hydrobromide in 250 mL of ethanol is then quickly added and the resulting suspension is stirred at a temperature of about 20° C. for 18 hours. The reaction medium is then concentrated under reduced pressure (2 kPa) at a temperature of about 40° C. The residue is taken up in 200 mL of distilled water and is neutralized with 1N aqueous hydrochloric acid until the pH is equal to 7. The obtained suspension is cooled at a temperature of about 0° C., filtered and the insoluble material is washed with 2 times 50 mL of ice-cold water, then dried in an oven under reduced pressure (10 kPa) at a temperature of about 40° C. for 18 hours. Thus 49.4 g of diethyl 2-(acetylamino)-2-(4-pyridinylmethyl) malonate is obtained in the form of a white-pinkish solid. [Infrared spectrum $CH_2Cl_2$: 3409; 2895; 1741; 1681; 1603; 1496; 1302; 1198; 1057; 855; 557 and 524 cm$^{-1}$].

Hydrobromide of 4-bromomethyl-pyridine

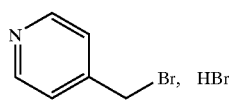

To a suspension of 140 g of triphenylphosphine bromide in 750 mL of dichloromethane, while stirring under an inert atmosphere, a solution of 30 g of 4-pyridyl-methanol in 250 mL of dichloromethane is added and this mixture is maintained at a temperature below 27° C. The reaction medium is stirred at a temperature of about 20° C. for 4 hours, then the insoluble material obtained is filtered, rinsed with 100 mL of dichloromethane and spin-filtered. Thus 61.5 g of hydrobromide of 4-bromethyl-pyridine is obtained in the form of a white solid. [Mass spectrum EI m/z=171 M$^+$; m/z=92 $C_6H_6N$; peak of base m/z=65 $C_5H_5^+$].

The pharmaceutical compositions according to the invention are formed with a compound of formula (I) or an isomer or a tautomer or a salt of such a compound, in pure form or in the form of a composition in which it is combined with any other pharmaceutically compatible product, which may be inert or physiologically active. The medicinal products according to the invention may be used orally, parenterally, rectally or topically.

Solid compositions for oral administration which can be used include tablets, pills, powders (gelatin capsules, cachets) or granules. In these compositions, the active principle according to the invention is mixed with one or more inert diluents, such as starch, cellulose, sucrose, lactose or silica, under a stream of argon. These compositions can also comprise substances other than diluents, for example one or more lubricants such as magnesium stearate or talc, a dye, a coating (dragées) or a varnish.

Liquid compositions for oral administration which can be used include pharmaceutically acceptable solutions, suspensions, emulsions, syrups and elixirs containing inert diluents such as water, ethanol, glycerol, plant oils or liquid paraffin. These compositions can comprise substances other than diluents, for example, wetting products, sweeteners, thickeners, flavorings or stabilizers.

The sterile compositions for parenteral administration can preferably be aqueous or non-aqueous solutions, suspensions or emulsions. Solvents or vehicles which may be used include water, propyleneglycol, polyethylene glycol, plant oils, in particular olive oil, injectable organic esters, for example, ethyl oleate, or other suitable organic solvents. These compositions can also contain adjuvants, in particular, wetting agents, isotonic agents, emulsifiers, dispersants and stabilizers. The sterilization can be carried out in several ways, for example, by aseptic filtration, by incorporing sterilizing agents into the composition, by irradiation or by heating. They can also be prepared in the form of sterile solid compositions which can be dissolved at the time of use in sterile water or any other injectable sterile medium The compositions for rectal administration are suppositories or rectal capsules which contain, besides the active product, excipients such as cocoa butter, semi-synthetic glycerides or polyethyleneglycols.

The compositions for topical administration can be, for example, creams, lotions, eye drops, mouth washes, nasal drops or aerosols.

In human therapy, the compounds according to the invention are particularly useful for treating and/or preventing multiple sclerosis, focal or global cerebral ischemia, cerebral or spinal trauma, Parkinson's disease, Huntington's disease, Alzheimer's disease, amyotrophic lateral sclerosis, migraine, depression, schizophrenia, anxiety, epilepsy, diabetes, atherosclerosis, myocarditis, arthritis, arthrosis, asthma, inflammatory bowel disease, Crohn's disease, peritonitis, gastro-esophageal reflux, uveitis, Guillain-Barré syndrome, glomerulo-nephritis, lupus erythematosus, psoriasis, the growth of certain forms of tumors such as, for example, epitheliomas, adenocarcinomas or sarcomas, and in infections with Gram-positive or Gram-negative intracellular or extracellular bacteria.

The doses depend on the desired effect, the duration of the treatment and the route of administration used; they generally comprise between 1 mg and 100 mg per day via the oral route for an adult, with unit doses ranging from 0.5 mg to 50 mg of active substance.

In general, the doctor will determine the appropriate dosage as a function of the age, weight and all the other personal factors of the individual to be treated.

The examples which follow illustrate compositions according to the invention:

EXAMPLE A

Gel capsules containing 50 mg of active product and having the composition below are prepared, according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium.stearate | 1 mg |

EXAMPLE B

Tablets containing 50 mg of active product and having the composition below are prepared, according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloïdal silica | 2 mg |
| Mixture of hydroxymethylcellulose, glycerol, titanium oxide (72–3, 5–24, 5) q.s. 1 finished film-coated tablet weighing 245 mg | |

EXAMPLE C

An injectible solution containing 10 mg of active product having the following composition:

| | | |
|---|---|---|
| Compound of formula (I) | | 10 mg |
| Benzoic acid | | 80 mg |
| Benzyl alcohol | | 0.06 ml |
| Sodium benzoate | | 80 mg |
| 95% ethanol | | 0.4 ml |
| Sodium hydroxide | | 24 mg |
| Propylene glycol | | 1.6 ml |
| Water | q.s | 4 ml |

The present invention also relates to the method for preventing and treating diseases in which an abnormal production of nitric oxide (NO) by induction of inducible NO-synthase (NOS-2 ou iNOS) is involved by administration of a compound of formula (I), the racemic mixtures, enantiomers, diastereoisomers thereof and mixtures thereof, tautomer thereof and pharmaceutically acceptable salts thereof.

We claim:

1. A compound of formula (I):

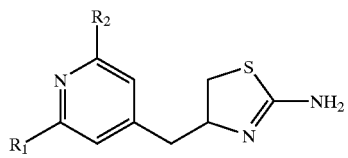

(I)

wherein $R_1$ and $R_2$ are the same and are selected from the group consisting of hydroxy, $(C_1-C_4)$alkyl, chlorine and $(C_1-C_4)$alkoxy; or at least one of $R_1$ or $R_2$ is a hydrogen and the other is a $(C_1-C_4)$alkyl, $(C_1-C_4)$alkoxy, hydroxy or chlorine; and wherein the $(C_1-C_4)$alkyl and $(C_1-C_4)$alkoxy contain 1 to 4 carbon atoms in straight or branched chain; or a racemate, an enantiomer, a diastereoisomer thereof or a mixture thereof or a tautomer thereof or a pharmaceutically acceptable salt thereof.

2. The compound according to claim 1, wherein $R_1$ and $R_2$ are chlorine.

3. The compound according to claim 1, wherein $R_1$ is hydrogen and $R_2$ is hydroxy or chlorine.

4. The compound according to claim 1, wherein the compound of formula (I) is chosen from the following compounds:

4-(2-hydroxy-pyridin-4-ylmethyl)-4,5-dihydro-1,3-thiazol-2-ylamine, 4-(2-chloro-pyridin-4-ylmethyl)-4,5-dihydro-1,3-thiazol-2-ylamine, and 4-(2,6-dichloro-pyridin-4-ylmethyl)-4,5-dihydro-1,3-thiazol-2-ylamine, or a racemate, an enantiomer, a diastereoisomer or a mixture thereof or a tautomer thereof or a pharmaceutically acceptable salt thereof.

5. The compound according to claim 4, wherein the compound of formula (I) is (+)-4-(2-hydroxy-pyridin-4-ylmethyl)-4,5-1,3-dihydro-thiazol-2-ylamine, or a tautomer thereof or a pharmaceutically acceptable salt thereof.

6. A pharmaceutical composition comprising, as active ingredient, at least one compound of formula (I):

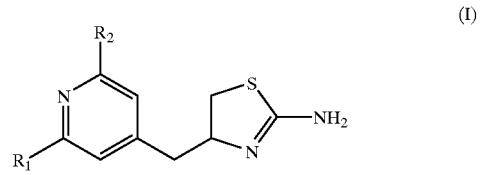

(I)

wherein $R_1$ and $R_2$ are the same and are selected from the group consisting of hydroxy, $(C_1-C_4)$alkyl, chlorine and $(C_1-C_4)$alkoxy; or at least one of $R_1$ or $R_2$ is a hydrogen and the other is a $(C_1-C_4)$alkyl, $(C_1-C_4)$alkoxy, hydroxy or chlorine; and wherein the $(C_1-C_4)$alkyl and $(C_1-C_4)$alkoxy contain 1 to 4 carbon atoms in straight or branched chain; or a racemate, an enantiomer, a diastereoisomer thereof or a mixture thereof or a tautomer thereof or a pharmaceutically acceptable salt thereof, optionally in combination with a pharmaceutically acceptable carrier.

7. The composition according to claim 6, wherein $R_1$ and $R_2$ are chlorine.

8. The composition according to claim 6, wherein $R_1$ is hydrogen and $R_2$ is hydroxy or chlorine.

9. The composition according to claim 6, wherein the compound of formula (I) is chosen from the following compounds:

4-(2-hydroxy-pyridin-4-ylmethyl)-4,5-dihydro-1,3-thiazol-2-ylamine, 4-(2-chloro-pyridin-4-ylmethyl)-4,5-dihydro-1,3-thiazol-2-ylamine, and 4-(2,6-dichloro-pyridin-4-ylmethyl)-4,5-dihydro-1,3-thiazol-2-ylamine, or a racemate, an enantiomer, a diastereoisomer or a mixture thereof or a tautomer thereof or a pharmaceutically acceptable salt thereof.

10. The composition according to claim 9, wherein the compound of formula (I) is (+)-4-(2-hydroxy-pyridin-4-ylmethyl)-4,5-dihydro-1,3-thiazol-2-ylamine or a tautomer thereof or a pharmaceutically acceptable salt thereof.

* * * * *